(12) United States Patent
Fredriksson et al.

(10) Patent No.: US 8,557,289 B2
(45) Date of Patent: Oct. 15, 2013

(54) NANOPARTICLE SUITABLE FOR DELIVERY OF A BIOMOLECULE INTO OR OUT OF A MEMBRANE ENCLOSED CELL OR CELL ORGANELLE

(75) Inventors: Sarah Fredriksson, Genarp (SE); Sylvia Koivunen, Helsingborg (SE); Fredrik Olsson, Malmö (SE); Hanna-Karin Toftevall, Eslöv (SE)

(73) Assignee: Genovis AB, Lund (SE)

( * ) Notice: Subject to any disclaimer, the term of this patent is extended or adjusted under 35 U.S.C. 154(b) by 773 days.

(21) Appl. No.: 11/990,522

(22) PCT Filed: Aug. 21, 2006

(86) PCT No.: PCT/SE2006/000960
§ 371 (c)(1),
(2), (4) Date: Mar. 26, 2008

(87) PCT Pub. No.: WO2007/021236
PCT Pub. Date: Feb. 22, 2007

(65) Prior Publication Data
US 2009/0304796 A1 Dec. 10, 2009

Related U.S. Application Data

(60) Provisional application No. 60/709,454, filed on Aug. 19, 2005.

(51) Int. Cl.
*A61K 9/14* (2006.01)
*A61K 48/00* (2006.01)

(52) U.S. Cl.
USPC .......................................... 424/489; 514/44 R

(58) Field of Classification Search
None
See application file for complete search history.

(56) References Cited

U.S. PATENT DOCUMENTS

| | | | |
|---|---|---|---|
| 5,928,958 | A | 7/1999 | Pilgrimm |
| 6,997,863 | B2 * | 2/2006 | Handy et al. ............ 600/9 |
| 2003/0032995 | A1 | 2/2003 | Handy et al. |
| 2003/0211045 | A1 | 11/2003 | Leszcyznska et al. |

FOREIGN PATENT DOCUMENTS

| | | |
|---|---|---|
| JP | 10-503281 | 3/1998 |
| WO | WO01/18168 A1 | 3/2001 |
| WO | WO 03/104385 A1 | 12/2003 |
| WO | WO2004/024910 A1 | 3/2004 |
| WO | WO2005/013897 A2 | 2/2005 |
| WO | WO2005/065282 A2 | 7/2005 |
| WO | 2005070471 A2 | 8/2005 |

OTHER PUBLICATIONS

Gupta, A.K. et al, "Synthesis and surface engineering of iron oxide nanoparticles for biomedical applications", Biomaterials, 2005, vol. 26, No. 18, pp. 3995-4021.
English-language translation of Official Action issued by South Korean Patent Office on Dec. 7, 2012 in South Korean Application No. 10-2008-7006690 (9 pgs).
Extended European Search Report issued by European Patent Office on Feb. 7, 2013 in European Application No. 06784101.5 (11 pgs).
M. Babincova et al. "AC-Magnetic Field Controlled Drug Release from Magnetoliposomes: Design of a Method for Site-specific Chemotherapy", Bioelectrochemistry, vol. 55, No. 1-2, Jan. 1, 2002, pp. 17-19.
N. Nitin et al "Functionalization and Peptide-Based Delivery of Magnetic Nanoparticles as an Intracellular MRI Contrast Agent", JBIC. Journal of Biological Inorganic Chemistry, Springer, DE, vol. 9, No. 6, Jun. 30, 2004, pp. 707-712.
M. Babincova et al. "Principles of Magnetodynamic Chemotherapy", Medical Hypotheses, Eden Press, Penrith, US, vol. 62, Jan. 1, 2004, pp. 375-377.

\* cited by examiner

*Primary Examiner* — Robert M Kelly
(74) *Attorney, Agent, or Firm* — Buchanan Ingersoll & Rooney P.C.

(57) ABSTRACT

A nano sized particle for in vitro or ex vivo biomolecule delivery to cell cultures through heat induced endosomal release comprising a superparamagnetic core coated in a heat sensitive coating, comprising membrane disruptive components and binding sites for attachment of biomolecules and markers to be delivered is provided. A method is provided for introducing the release effect of a plurality of said biomolecule and endosomal disrupture molecules by applying an alternating field to a cell culture harboring the particle described by the invention.

8 Claims, 7 Drawing Sheets

| Sample | FT | W1 | W2 | W3 | E |
|---|---|---|---|---|---|
| 1 | 1402 | 18480 | 1499 | 1428 | 53831 |
| 2 | 23 | 3229 | 0 | 0 | 52307 |
| 3 | 6795 | 62498 | 0 | 0 | 0 |
| 4 | 191 | 2826 | 61 | 8 | 60247 |
| 5 | 1009 | 13937 | 473 | 193 | 56951 |
| 6 | 7235 | 37780 | 229 | 0 | 59248 |
| 7 | 2084 | 23960 | 0 | 0 | 0 |

US 8,557,289 B2

NANOPARTICLE SUITABLE FOR DELIVERY OF A BIOMOLECULE INTO OR OUT OF A MEMBRANE ENCLOSED CELL OR CELL ORGANELLE

This is a 35 U.S.C.§371 filing of International Patent Application No. PCT/SE2006/000960, filed Aug. 21, 2006. The benefit is claimed under 35 U.S.C.§119(e) of U.S. Provisional Application No. 60/709,454 filed Aug. 19, 2005.

TECHNICAL FIELD OF THE INVENTION

The present invention relates to a particle suitable for the delivery of a substance into or out of a membrane enclosed cell or cell organelle through heat induced release of said substance, to the use of said particle in different applications as well as a method of delivering a substance into or out of a membrane enclosed cell or cell organelle through heat induced release of said substance.

BACKGROUND OF THE INVENTION

Reliable biomolecule delivery methods are indispensable tools for many Life Scientists. Transfection, siRNA evaluation and screening of various cell labeling methods are examples where efficient delivery to the target cell culture is crucial. Successful biomolecule non-viral delivery methods for in vitro purposes have to overcome a series of hindrance and avoid toxic effects on the target cell and still efficiently deliver functional biomolecules of choice within the cell. The first step in the delivery process is for the biomolecule to reach the surfaces of the target cells. The biomolecule should be delivered to the cell independent of media components in the cell culture and reach both adherent cell lines and cells in suspension. Once delivered at the cell surface the biomolecule has to either transverse the cell membrane/cell wall or enter the cell through an endocytosis pathway. Once within the endosome pH is low and both the cytosol and the endosome contain various degrading enzymes. Efficient delivery methods should preferably minimize cellular degrading of the biomolecule in question, whether it constitutes a DNA, RNA, protein or other molecule. To achieve a successful delivery process where the biomolecule enter the cell through endocytosis it is desirable to promote endosomal release into the cytosol of as many biomolecules as possible from each endosomal compartment. Once in the cytosol the biomolecule should preferably be targeted to a special intracellular compartment such as for instance the cell nucleus.

The basic technologies for all non-viral biomolecule delivery methods available today can be divided into two approaches. Physical methods like electroporation, microinjection and gene bombardment which deliver the biomolecule through the cell membrane into the cytosol. The chemical/synthetical methods use the target cell endocytosis. Both technologies have specific features as well as limitations and are well established methods.

The increased number of high throughput preclinical cell based in vitro studies on stem cells, primary cell lines as well as cultured standard laboratory cell lines requires efficient, robust and cost effective biomolecule delivery methods. To meet these needs it is desirable to improve delivery efficiency of chemical and synthetic delivery method. One approach to increase the efficiency is to actively promote endosomal release.

SUMMARY OF THE INVENTION

The present invention relates in one aspect to a particle suitable for the delivery of a substance into or out of a membrane enclosed cell or cell organelle through heat induced release of said substance comprising: a superparamagnetic core capable of generating heat in a magnetic alternating field encapsulated in a heat sensitive coating whereto said substance and a membrane disruptive agent are associated.

The invention in a further aspect relates to the use of a particle for modifying the genetic code and/or metabolism of the host cell.

In a yet further aspect the invention relates to the use of a particle for releasing said substance from endosomal or lysosomal organelles.

In a yet further aspect the invention relates to a method of delivering a substance into or out of a membrane enclosed cell or cell organelle through heat induced release of said substance in combination with heat induced release of a membrane disruptive agent comprising:
  providing a sample comprising membrane enclosed cells or cell organelles and a plurality of particles according to the invention;
  applying a magnetic alternating field to said sample, whereby thermal energy of the particle core causes the heat sensitive coating of said particle to decompose, which cause the disruptive agent to disrupt the membrane of the enclosed cell or cell organelle and release said substance.

BRIEF DESCRIPTION OF THE DRAWINGS

FIG. 4: Result from the test on high gradient magnetic separation of cells treated with particle as described in example 5.

DETAILED DESCRIPTION OF THE INVENTION

Figure 1:
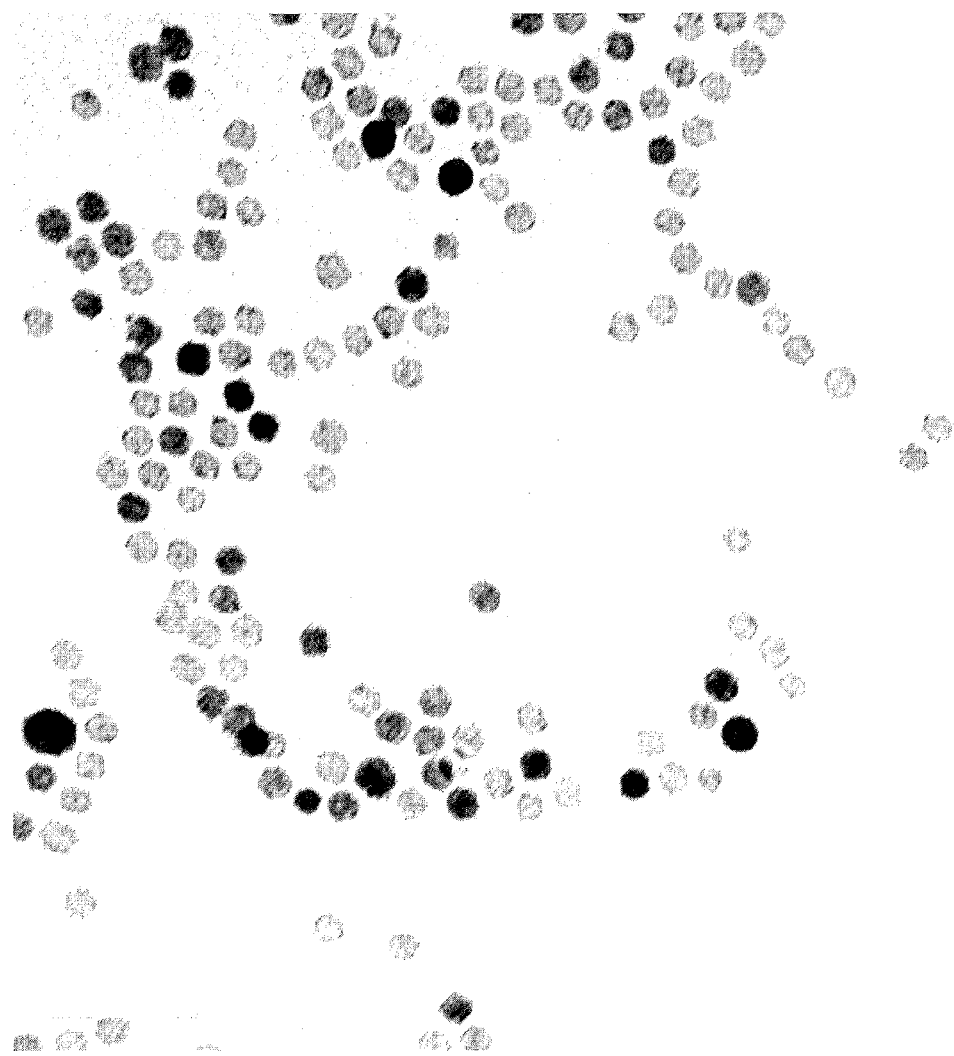
FIG. 1: TEM image of an example of iron oxide core of the described nanoparticle.

With the foregoing in mind, the present invention provides a particle suitable for biomolecule delivery, which combine endosomal release within a diversity of possible target cells with delivery of a variaty of biomolecules with a high efficiency.

The present invention will now be described more fully hereinafter with references to the accompanying drawings, in which preferred embodiments of the invention are shown. This invention may, however, be embodied in many different forms and should not be construed as limited to the illustrated embodiments set forth herein. Rather, these embodiments are provided so that this disclosure will be thorough and will fully convey the scope of the invention to those skilled in the art.

We have earlier described in WO 01/18168 a method for introduction or extraction of bioparticles into or from biological membrane-enveloped structures by applying an alternating magnetic field to a sample of superparamagneic particles attached to the membrane enclosed cell or organelle, whereby an increase in the thermal energy causes heating of the superparamagnetic core of the particle, which in turn causes temporary openings in the cell membrane or organelle membrane.

The invention described here is a particle designed for biomolecule delivery in vitro or ex vivo which make use of the thermal energy released from the superparamagnetic core upon exposure to an alternating magnetic field to release membrane disruptive molecules such as lipids, cholesterol or detergents from the heat sensitive coating of said particle in order to induce chemical membrane disrupture. Both the substance (e.g. a biomolecule) that is to be delivered (herinafter called cargo molecule) and molecules that can promote disruption of cell or organelle membranes like endosome membrane are released during the heating of the superparamagnetic core of said particle. In the context of the present application the terms "substance" and "cargo molecule" are used interchangeably. The substances or cargo molecules are delivered to the target cells through the particles of the invention. An example of a substance or cargo molecule is a biomolecule.

Applications of magnetic particles in biomedicine and biotechnology are continuously growing. Today magnetic nanoparticles are used for purification, quantification, transfection, hyperthermia, drug delivery, imaging by MRI among others. Superparamagnetic particles entrapped together with prodrugs inside liposomes for drug delivery purposes have been described in US2003211045, where heating of the magnetic particles inside the liposomes will convert the prodrug into drug. Yet another particle where superparamagnetic cores are incapsulted in organic compounds and vesicle forming lipids are described in U.S. Pat. No. 5,441,746, where the particles are intented for inductive heating of the superparamagnetic core to promote killing of cancer cells.

In contrast to these earlier described lipid encapsulated superparamagnetic cores the present invention describes a superparamagnetic particle that in addition to generating heat in an alternating magnetic field is designated for non-viral biomolecule delivery in vitro or ex vivo. In addition to carrying the cargo molecule to the cell surface where the particle/cargo molecule complex is taken up by the cell through endocytosis, the particle is enhancing endosomal release of the cargo molecule when exposed to an alternating magnetic field. The surface of the particle is hence not homogenous, but instead carries a combination of heat sensitive structures that will be released or change configuration upon pulses of heating. Each particle of plurality described by the invention carries multiple coupling and or attachment sites for the cargo molecule, one or more membrane disrupting agents, recognition molecules which can recognize and bind to the target cells and signal-molecules (such as peptides) and fluorescent markers for imaging of the delivery process.

In an embodiment of the invention the size of the superparamagnetic core is between 1 and 100 nm, preferably between 8 and 15 nanometers.

In a further embodiment of the invention said superparamagnetic core consists of magnetite, maghemite, ironoxide-hydrate, ferrites of the general formula $MeOxFe_2O_3$ where Me is a bivalent metal selected from the group consisting of Co, Ni, Mn, Be, Mg, Ca, Ba, Sr, Cu, Zn, Pt, Al, Cr, Bi and combinations thereof.

In a further embodiment of the invention the heat sensitive coating comprises a micelle like structure in direct contact with said core, wherein said micelle like structure is built up by at least one hydrophobic molecule and at least one molecule containing both an hydrophobic and a hydrophilic moiety. The heat sensitive coating is attached to said substance and membrane disruptive agent with single or multiple disulfide bonds, peroxide bonds or azo bonds or combinations thereof.

In an embodiment of the invention said hydrophilic moiety structure contains polymers, lipids, synthetic molecules, proteins or combinations thereof.

In a yet further embodiment of the invention at least one recognition molecule is also associated to the heat sensitive coating, wherein said recognition molecule is chosen from the group consisting of antibodies, fragments of antibodies and lectins.

In a further embodiment of the invention the membrane disruptive agent is chosen from the group consisting of detergents, cholesterol, hydrophobic proteins and surfactants and mixtures thereof.

In a further embodiment of the invention said substances or cargo molecules are selected from the group consisting of DNA molecules, RNA molecules, proteins, peptides, lipids, chemical preparations, organic compounds, detergents, synthetic polymers and combinations thereof.

In an embodiment of the method of the invention said magnetic field has an alternating field direction of a frequency in the range of 0.1 to 5 MHz. The magnetic field may have a field strength in the range of 1 to 100 mT.

In a yet further embodiment of the invention said magnetic field is exposed repeatedly as a series of pulses over time each pulse duration preferably between 1 and 600 s, and even more preferably between 1 and 45 seconds. The magnetic field may have an alternating field which is non-homogeneous and has an alternating gradient field direction, the direction of said alternating magnetic field being generated by two coils, and said sample is inserted between the coils. The coils may be supplied with either the positive or negative part of the supplied alternating current.

The present invention constitutes a superparamagnetic core encapsulated in coating layer or layers, where the inner layer is in direct contact with the superparamagnetic core, see example 1 and 2. The superparamagnetic core of the particle fulfils three desirable features; it is traceable using MRI, cells harbouring such particles can be sorted using magnetic separation technologies, see example 2 and 5 and most important; it can be made to generate heat. An alternating magnetic field induces heat within the magnetic core of each particle due to both a rotation of the particle and to a rotation of the magnetic momentum within the particle, see example 3. Both of these phenomenon result in heat losses. Which one of them that dominates in a given moment depends on the particle size, field frequency and particle coating. The preferred size of the core of the particle is between 8 and 15 nanometer, since cores in this size interval makes it possible to use frequencies in the lower mega hertz range of the alternating magnetic field and hence avoid eddy heating of target cells and surrounding growth media. The coating of the particles should be kept as thin as possible to keep the size of the particle as a whole preferably below 50 nanometers. Small particles promote high surfaces and advantageous kinetics for binding to various cell surface, see example 10. If the particle is small enough not to precipate in a test tube due to gravity it is capable of interacting with both cells in suspension and adherent cell lines.

The coating of the particle is of great importance to keep the particles well separated from each other in a stable colloidal solution. The stability in various buffers and cell culture media is crucial for the usefulness and effectiveness of the nanoparticle both in terms of surface modification, using various biochemical coupling technologies, as well as in terms of the effect on living cells. For coupling chemistry of the cargo molecule and/or cell recognition molecules to the surface of the particle amino-PEG can be introduced on the surface of the particles enabling coupling by NHS(N-hudroxysulfosuccinimide ester), SPDP(N-succinimidyl 3-(2 pyridyldithio)propionate), glutaric aldehyde and other bioconjugate techniques. The cargo molecule to be delivered to cells in vitro or ex vivo is attached to the coating covalently, electrostatically or through van der Waals interactions. In the case of the cargo molecule being a DNA or RNA molecule electrostatic interactions between the negative backbone of DNA or RNA molecules and positively charged molecules like DOTAB integrated within the outer layer of the coating or positively charged molecules like polylysin, PEI (polyetylenimin), protamine, arginin- or lysine rich peptides covalently coupled to a amino-PEG molecule in the outer surface layer of the heat sensitive coating is readily utilized. Additional molecules like florescent markers or target cell recognition molecules are attached by the same procedures as the cargo molecule.

When the particle is complex bound with a cargo molecule, like DNA or RNA molecules for gene transfer purposes, the particle should serve as a stable and non-toxic carrier. Additionally, the particles should preferably protect their cargomolecules from degradation as well as promote release of the very same molecule at the target site within the cell. By complexing the cargo molecule close to the particle surface a steric hindrance for degrading enzymes is introduced which in turn is favourable to prevent enzymatic degradation of the cargo molecule.

In addition to cargo molecules the nanoparticle can carry signal-molecules (such as peptides) and fluorescent markers. The present invention can, in addition to carrying different cargo molecules, induce a heat release effect from the surface of the nanoparticle. The idea behind heat induced delivery is to increase the rate of molecular diffusion in close vicinity to the particle and to promote the release of molecules attached to the surface of the particles.

Two layers of molecules build up the coating. The inner layer consists of a hydrophobic molecule, for instance a fatty acid like oleic acid, or a mixture of hydrophobic molecules. The second layer consists of a mixture of molecules each of them is characterized by one hydrophobic part and a hydrophilic part. The hydrophobic part is building up a double layer, a micelle like structure, with the first layer while the hydrophilic part is directed outward into the surrounding media giving the particle stability in water based buffers and growth media. This hydrophilic part is further utilized to attach the cargo molecule and any recognition molecule or signal molecule additionally attached to the surface of the particle coating.

When exposing the coating to temperatures corresponding to the coating lipids transition temperatures the coating described above is responding with interior molecular rearrangements or disruptions due to leading to a leakage of the coating from the particle, which in turn releases the substances attached to said coating. The phase transition temperature is defined as the temperature required to induce a change in the lipid physical state from the ordered gel phase, where the hydrocarbon chains are fully extended and closely packed, to the disordered liquid crystalline phase, where the hydrocarbon chains are randomly oriented and fluid. There are several factors, which directly affect the phase transition temperature including hydrocarbon length, unsaturation, charge, and head group species.

Since the superparamagnetic core of the particle can be made to generate heat within an alternating field, the heating procedure can be made very precise in volume in very close vicinity to the particle. The target cell as a whole will hence not be heated.

By including various molecules in the outer lipid layer a multipurpose heat release nanoparticle is built up. Known helper molecules like cholesterol, DOPE (dioleoyl-phosphatidylethanolamine) lipids is transported as parts/members of the surface outer layer. Detergents like Triton X and SDS (sodium dodecyl sulfate) and similar molecules can also be parts/members of the outer coating layer. When these detergents are integrated in the particle they are less toxic to the target cells, but when released from the particle they are promoting disrupture of endosomal membrane(s), see further in example 11. In addition, by choosing temperature sensitive covalent bridges between molecules in the outer coating layer and the cargo molecules it is possible to even more strongly promote the release of the cargo molecule from the nanoparticle for subsequent escape from the endosomal compartment, see example 4 and 6.

In one embodiment of the invention described is a method where the particle according to the described invention is used for substance delivery into cell cultures in vitro or ex vivo. The desired substance or substances is bound to the surface of the particle through electrostatic interactions, covalently or through van der Waal interactions as a cargo molecule. The particle/cargo molecule complexes are mixed with the cell growth medium. The surface of the particle may carry affinity molecules that can bind to certain targets on the surface of the target cells or have a net positive charge which promote the particle/cargo complex to interact with the target cells negative surface areas. The particle is rapidly encapsulated by endocytos by the target cells and the early endosomes can then be transported into the cells and subsequently processed by the cells into late endosomes and transported to Golgi and endoplasmatic reticulum organelle compartments within the cells. The magnetic field is then applied in pulses of a few seconds to minutes with pauses of equal time durations. Two to hundreds of pulses can be applied and the repeated heating cause leaking from the particle coating molecules and hence a release of both cargo molecule associated them and membrane disruptive molecules. Membrane disruptive agents insert themselves in the endosomal membrane and hence causing rupture of the endosomes. If the cargo molecule is covalently coupled to the particle coating a heat sensitive covalent bond like for instance a disulfide bridge, can promote the release effect additionally when heated upon. The incubation time of cells and particle before exposure to the magnetic field have an impact on the delivery procedure and is individually optimized for each specific cell line. In addition the magnetic field can be applied more than one occasion to improve the delivery process over time with an incubation time of a less than an hour to several hours in between each treatment.

Treated cells are automatically labeled and traceable in MRI and in addition fluorescent markers can be added to the particle coating to provide the possibility to follow the procedure in a florescent microscope. In addition a the cells can be washed and sorted using high gradient magnetic field separation methods at any time and cells can be moved under a microscope when exposed to movements of a permanent magnet.

EXAMPLE 1

Thermal Decomposition of Iron Carboxylate Salt

For production of monodisperse particles 11±1 nm the following procedure was used. 360 mg of Iron (III) Oxide was grounded to smaller particles and added to 5 g of oleic acid and 11 g of 1-Octadecene. The solution is mixed and transferred to a three neck bottle flask, placed in a heating mantel with magnetic stirrer and heated until temperature reaches at least 320° C. and 1-Octadecen starts boiling. During a one hour reaction time temperature is monitored and should preferably not drop down below the above mentioned temperature. After one hour incubation the solution was allowed to cool to room temperature. Particles are purified from excess reagents by washing repeatedly with ethanol, methanol, chloroform or a combination thereof and finally resuspended in chloroform or hexane.

EXAMPLE 2

Poly(ethyleneglycol)-lipid Surface Coating

Briefly, particles were suspended in chloroform, and subsequentially dried under vacuum. A chloroform solution containing between 30-60% mol phospholipids (e.g 1,2-Dipalmitoyl-sn-Glycero-3-Phosphocholine or others similar in chemical structure) and 40% mol or more PEG-lipid (e.g 1,2-Dipalmitoyl-sn-Glycero-3-Phosphoethanolamine-N-[Methoxy(Polyethylene glycol)-2000], 1,2-Distearoyl-sn-Glycero-3-Phosphoethanolamine-N-[Amino(Polyethylene Glycol)2000] or similar PEG-lipids, or others similar in chemical structure) are added to the dried particles which then returns to solution. Chloroform is evaporated and particles are further dried for 1-4 hours. Particles are then hydrated using water, NaCl or common physiological buffer and mildly sonicated to receive a clear solution that can be sterile filtered through a 100 nm filter. Particles are purified from lipids and PEG-lipids by high gradient magnetic separation and stored at 4° C. However, particles may be stored at room temperature for weeks without noticeable change in properties. Particles remain colloidal stable for weeks in common buffers with physiological salt concentrations. Particles remain stable even in complex growth media containing 10% FCS (serum) for more than 3 days although upper time limits have not been tested, they may stay in solution for even longer time periods.

The particle suspension was easily purified from coupling chemicals and/or salts by filtration through a magnetic column (magnetic high gradient separation) or by size exclusion chromatography.

Magnetic High Gradient Separation Column

The particle suspension is applied to a column containing a magnetic matrix, which was exposed to a high permanent magnetic field of 1.2 T. The particles are retained in the magnetic matrix as long as the matrix is exposed to a high magnetic field. When the magnetic field was removed the particles was eluted with water or desired buffer solution. It was also possible to concentrate the ferrofluid on the magnetic column by eluting a smaller volume.

Size Exclusion Chromatography

The particle suspension is applied to a column packed with Sephacryl™ S-500 High Resolution gel. The ferrofluid is separated from coupling chemicals and/or salts by size exclusion. The ferrofluid is eluted with water or desired buffer solution.

Size and Stability

The average diameter of the iron oxide cores of the particles was estimated to 11±1 nm using TEM (trans electron microscope), see FIG. 1. The diameter of the whole particle varies depending on composition of the surface layer of lipids and characteristics of the carrier liquid. The magnetic nanosparticles are easily sterile filtered and colloidal stable in common physiological buffers and hence it was possible to utilize size exclusion chromatography, dialysis and high magnetic field separation during the process of production and further modification of the particles. The amino groups on the surface of the particles were analysed using Fluram® with a standard protocol and the amount of amino groups could be varied between a few hundred up to several thousands amino groups per particle without affecting the stability of the particles. Furthermore, the amino groups are accessible to covalent coupling using common and well-established coupling chemistry for addition of other functional groups or molecules.

EXAMPLE 3

Heat Losses in Alternating Magnetic Fields

Figure 2A:
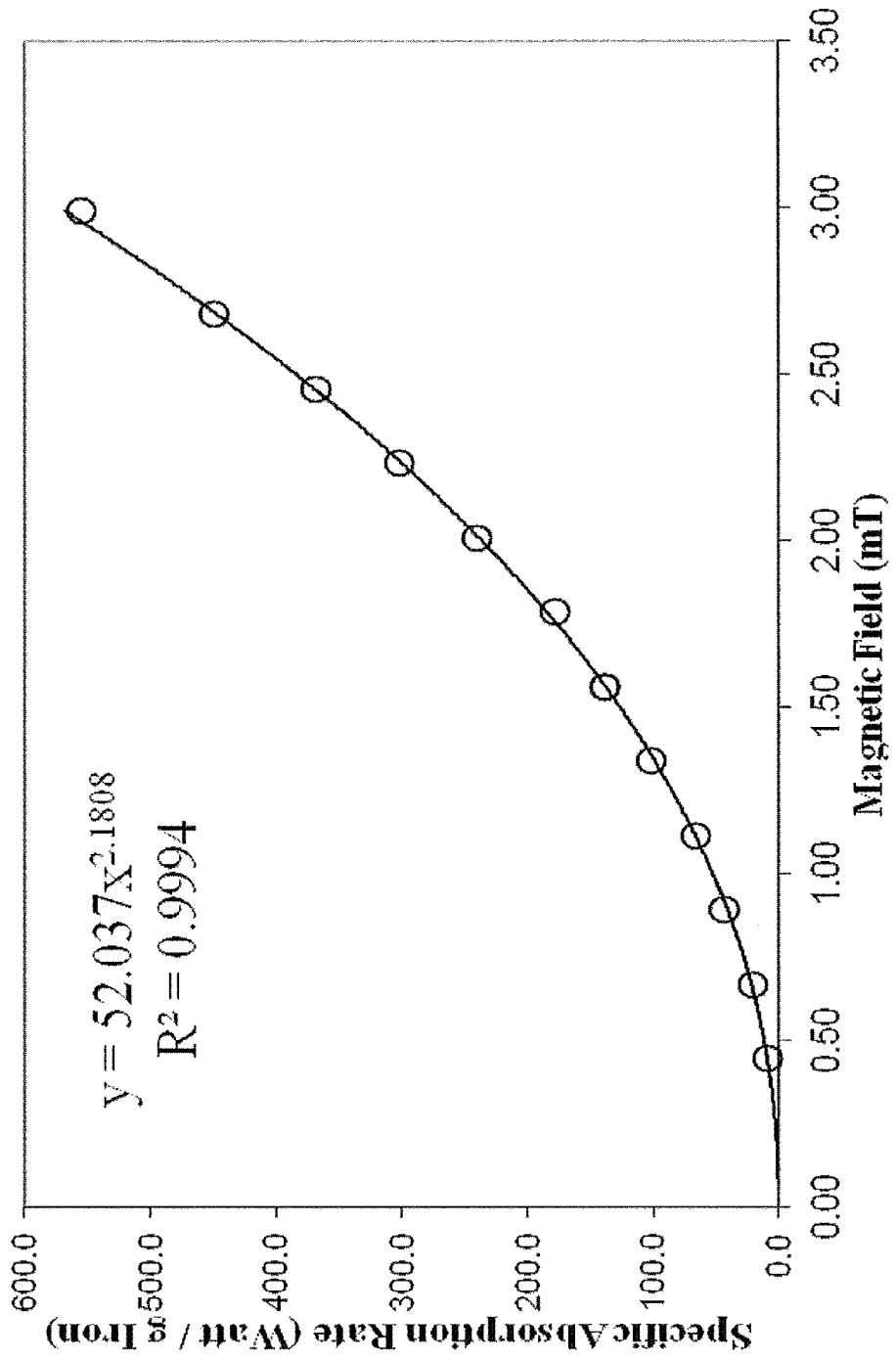
FIG. 2 Heat effects (A) The relation between the specific absorption rate (SAR-value) of the nanoparticles and the applied magnetic field strength in an alternating field with the frequency of 10 MHz. (B) This graph illustrates the increase in temperature within a 100 µl sample of 7 mg Fe/ml in 0.15 M NaCl subjected to an alternating magnetic field of 10 MHz, 2.9 mT. The values have been corrected for the temperature increase in a reference sample without particles. Temperature measurements were performed with a fiber optic probe (IPITEK)
Figure 2B:
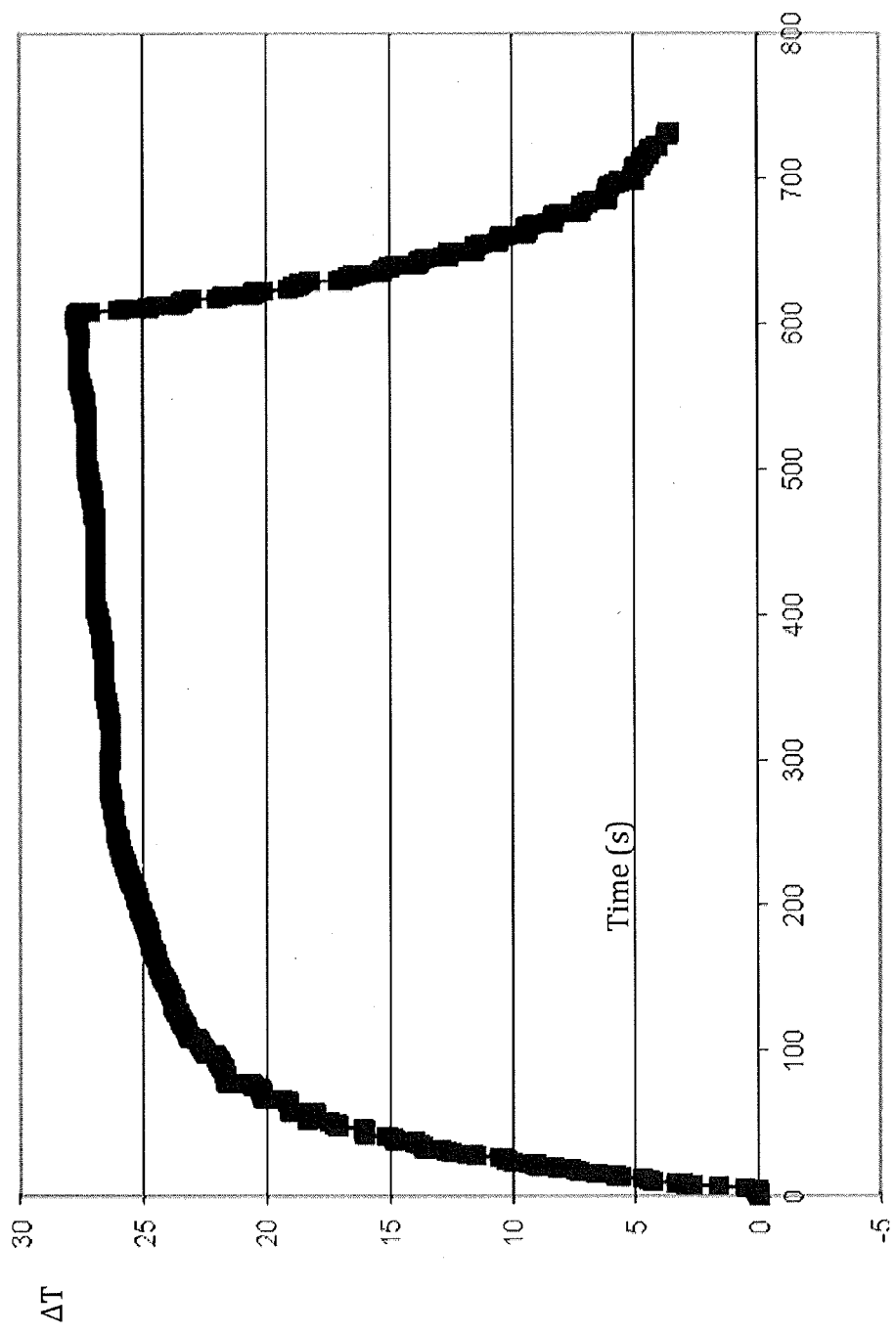

The cores of the particles are superparamagnetic and when such a particle is subjected to an alternating magnetic field heat is lost to the surrounding medium. The frequency dependence of the specific absorption rate (SAR) of the particles was tested and evaluated. SAR values of more than 500 watt/g was achieved at a frequency of 10 MHz and field strength of 2.8 mT, as illustrated in FIG. 2.

EXAMPLE 4

The Effect of Heat on Release of Molecules from the Surface of the Particles

Samples containing particles carrying phospholipids and amino-PEG-lipids with the amino groups fluorescently labeled with Fluram® were treated for 5 min in 10 MHz, 2.9 mT followed by magnetic separation to get a first indication on the heat on the surface of the particles and possible heat release in the magnetic field. In comparison tests were also done with 5 min treatment of samples in temperatures ranging from 40 to 95° C. in a conventional water bath. The release of Fluram®-labeled amino groups was measured in the flow through from magnetic separation of the particles.

The results can be summarized as follows:
1. Between 2 and 6% of the amino groups are released from the particle upon heating.
2. The amount of released group peaked between 50-60° C. and then the amount of release decreased at higher temperatures.
3. The sample treated 5 min in the magnetic field released between 2 and 3% of the amino groups.

The amino-PEG-nn leaves the particle at relatively low temperature increases. This feature makes the particle suitable for slow release. If a molecule is coupled covalently to the amino group a slow and repeated release can be performed with a repeated treatment in an alternating magnetic field.

EXAMPLE 5

To find out if both the amino-PEG-nn and the phospholipids are released at the same rate and temperature samples with particles carrying FITC labeled phospholipids were treated 5 min in temperatures ranging from 40 to 95° C. in a conventional water bath.

The results can be summarized as follows:
1. Up to 25% of the FITC labeled phospholipids are released from the particle upon heating above 80° C. for 5 minutes.
2. Samples treated at temperatures above 80° C. flocculated after treatment indicating colloidal instability.

This example illustrates that the phospholipids in comparison to the PEG-lipid is more reluctant to leave the iron oxide core and that heating above 80° C. has a severe impact on the colloidal stability of the particle suspension.

EXAMPLE 6

Samples with particles carrying FITC labeled HIV TAT-peptide covalently coupled to the amino groups on the surface of the particle were treated as described above. This example was set up to find out if the release effect can be increased by covalently creating a bond that is heat sensitive between the amino group and another molecule. The peptide was coupled to the particle with SPDP as mediator generating a disulfide bridge between the particle and the TAT-peptide. Disulfide bridges are known to be relatively heat sensitive.

The results can be summarized as follows:
1. Between 3 and 13% of the TAT-peptide was released from the particle upon heating.
2. The release effect increased with temperature. In comparison with the results presented in example 2 this is an increased release effect probably due to heat induced breakage of the disulfide bridges.
3. The samples treated with the magnetic field released between 3 and 5% of the TAT-peptides.

EXAMPLE 7

Cell Growth

The adherent cell line COS-7 was grown in DMEM, 10% FCS and 5% Streptomycin/penicillin. The suspension cell line K562 was grown in RPMI, 10% FCS and 5% $CO_2$. Cells were passaged two times per week.

Proliferation

Figure 3:
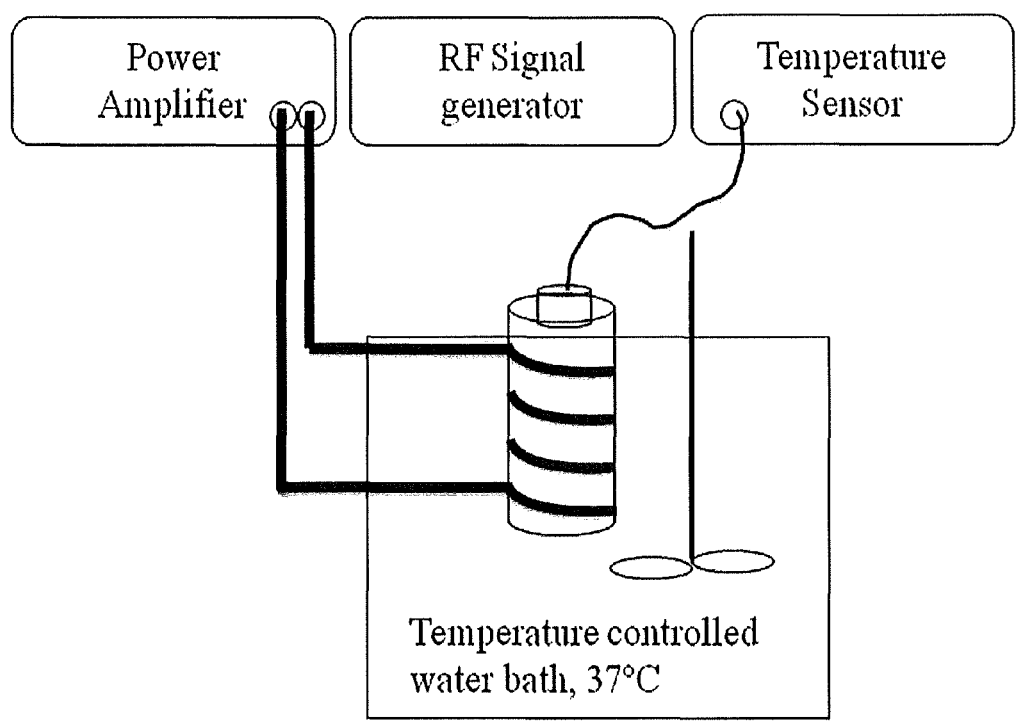
FIG. 3: Schematic illustration of experimental set-up.

COS-7 and K562 cells were harvested and seeded in a 96-well plate with $10^5$ cells per well in 100 µl complete DMEM or RPMI, respectively. Cells for a proliferation standard were seeded with $10^4$ to $10^5$ cells/well in triplicates. Particles with amino groups, linear PEI or branched PEI were diluted in an appropriate buffer to different Fe concentrations. Each dilution of the different particles was added in quadruples to the cells to give a final Fe concentration between 50 and 250 pg Fe per cell. Additionally, tests on COS-7 cell proliferation upon exposure of particle/cell complex to an alternating magnetic field 10 MHz, 2.9 mT were performed using a experimental setup illustrated in FIG. 3. A water bath was used to cool the coil and keep the sample at desired temperature. The temperature within the sample is continuously monitored using an optical fibre thermometer immune to RF magnetic field.

The proliferation assay was preformed after 24 hours incubation. It could be concluded that it seems like the proliferation decreases if the cells that carries relatively high concentrations of particles are exposed to an alternating magnetic field. Furthermore, modification of particles with PEI (polyethylenimin)renders them more toxic to cells, and K562 are more sensitive to the particles than COS-7.

EXAMPLE 8

Separation and Washing of Cells

K562 cells were seeded in a 24 well micrititer plate with 1 ml of medium per well. Particle carrying DOTAB/DOPE/phospholipids in mixed coating were added to the cells in the following concentrations:
Sample1: 1 picogram Fe/cell, incubated two hours
Sample2: 2 picogram Fe/cell, incubated two hours
Sample3: 2 picogram Fe/cell, incubated two hours, no magnet where used in separation coloumn.
Sample4: 2 picogram Fe/cell, incubated 24 hours
Sample5: 2 picogram Fe/cell, incubated 48 hours
Sample5: 2 picogram Fe/cell, incubated 72 hours
Sample7: 0 picogram Fe/cell, incubated two hours Cells were removed from the culture dishes and washed using short centrifugation in buffer (PBS+BSA). Live cells were marked with Calcein AM followed by subsequent washing and then applied to a high gradient magnetic separation coloumn (Milteyi). Each sample was treated in a coloumn, sample nr 3 was separated without applying the external static magnetic field. The cells were washed with three coloumn volumes of buffer and eluated by releasing the column from the permanent magnet according to suppliers manual. Calcein flourescens were detected in the various fractions.

Fractions:
Flow through (FT)
Washings 1, 2, 3 (W1, W2, W3)
Elution (E)

From the result presented in FIG. 4 it is clearly seen that addition of 2 picograms FE/cell is enough to give treated cell enough magnetic material to be able to use high gradient magnetic field for separation and washing and the effect is lasting for up to 72 hours.

EXAMPLE 9

Cellular Uptake and Distribution of Particles

Fluorescence microscopy of COS-7 cells incubated for 1 hour and 24 hours with superparamagnetic nanoparticles were utilized to follow the particles on there transport through the cell. It could be seen that the particles are readily and relatively quickly taken up by the cell and distributed evenly through the cell.

In another test COS-7 cells were incubated for 12 hours with magnetic nanoparticles (100 pg iron/cell) labelled with Texas-Red and covalently modified with a FITC labelled HIV-1 TAT-peptide. This peptide can in a native state target and enter the cell nucleus. Both the Texas-Red label (on the phospholipids) and the FITC labelled HIV-1 TAT-peptide co-localize in the cell cytoplasm.

EXAMPLE 10

Plasmid DNA Binding Capacity

Figure 5:
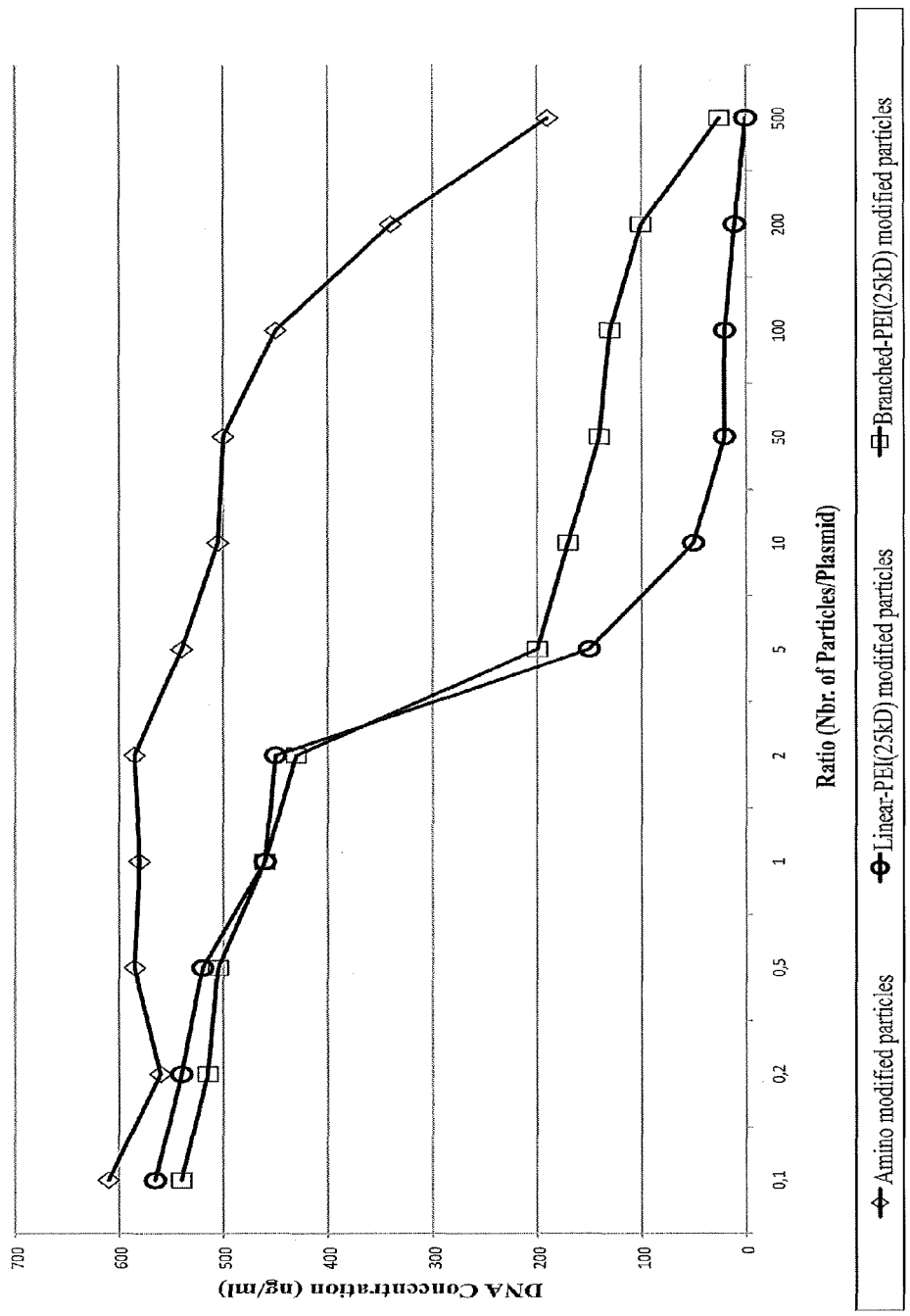
FIG. 5: Investigation of DNA binding capacity of themagnetic nanoparticles, surface-modified with amino groups, Linear PEI and Branched PEI. Different amounts of particles where incubated with plasmid DNA (phRLSV40-luc, 3.7 kb) for 10 minutes in TE buffer. After addition of PicoGreen fluorescence was measured using a microplate fluorescence reader equipped with a FITC filter. Reduced Fluorescence indicates condensed DNA.

Nanoparticles with or without covalently coupled linear PEI (polyethyleneimin) or branched PEI to the amino PEG on the particle surface was diluted in buffer to the same particle concentration. Particles were mixed with the same amount of DNA (100 ng) in different particle to DNA ratios (0.1-500). A DNA standard was prepared (10-500 ng/ml). The solutions were incubated 10 min in room temperature then PicoGreen® was added and fluorescence was measured (Ex 485/Em 520). The results are presented in FIG. 5 and it can be concluded that all of the particles were capable of binding DNA and that particles with surface that exposed branched PEI bound DNA most effectively.

EXAMPLE 11

Transfection with Particles Carrying a Mixture of SDS, DOPE and DOTAB in Comparison with Particles Carrying PEG-NH2 Only.

Cells (K562) were incubated for 3 hours together with particles with DOTAB/DOPE/SDS coating carrying texas red and plasmid coding for luciferase (phRL-SV40) and as a reference cells were incubated in the same way with particles with Amnio-PEG (NH2) coating carrying plasmid coding for luciferase (phRL-SV40). After incubation, cells were treated in AMF (alternating magnetic field) repeatedly with 30 second pulses and 30 second rest in between pulses.

Figure 6:
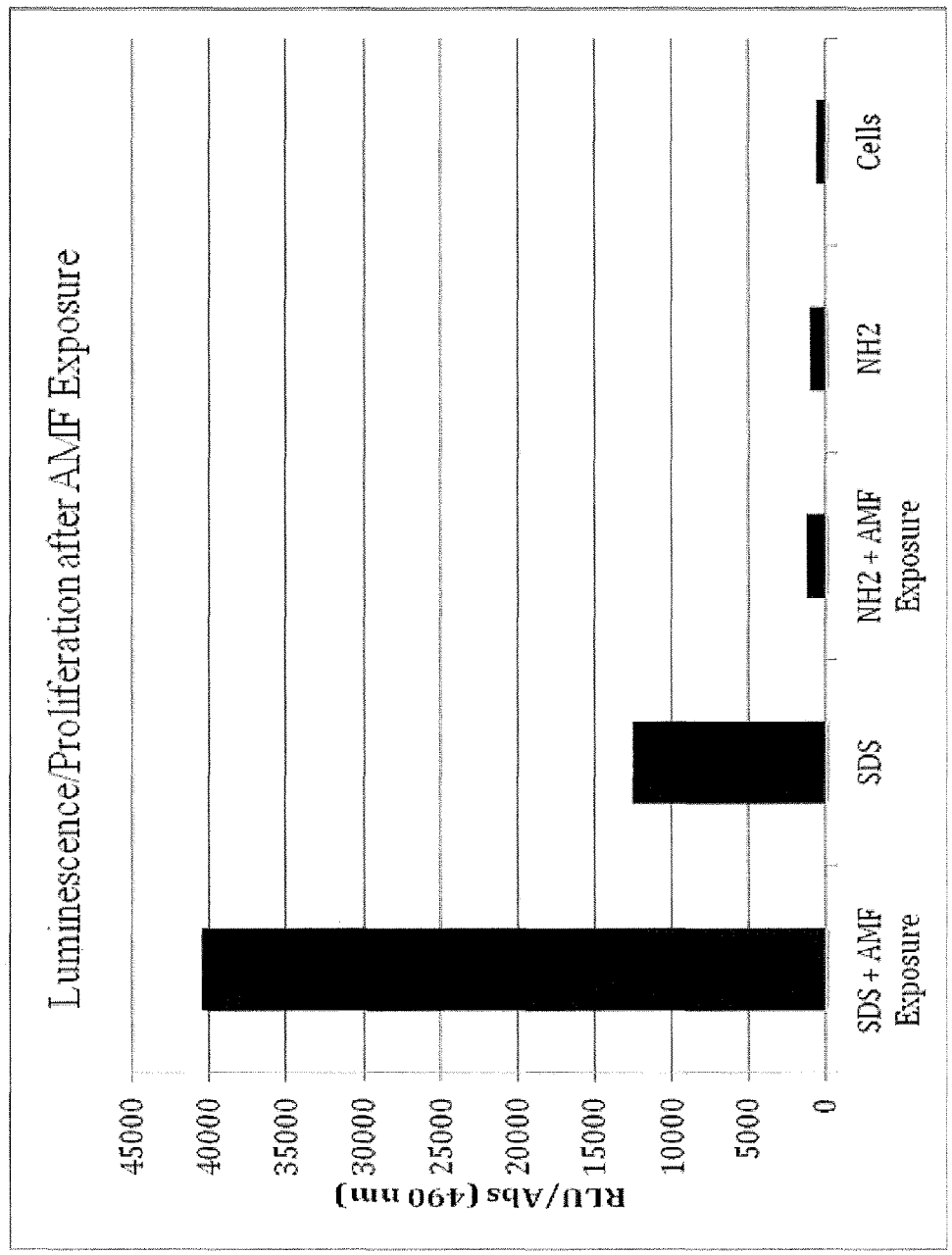
FIG. 6: Results from transfection of K562 cells as described in example 11. The sample marked as 'cells' is a control of background generated in cells not transfected.

After AMF exposure cells were seeded into new culture dishes and proliferation an luminescens were read after 48 hours post treatment. As seen in FIG. 6 the particles carrying detergent and helper lipids (DOTAB/DOPE/SDS) shows an substantially higher expression rate.

The invention claimed is:

1. An ex vivo method of delivering a DNA or RNA molecule into a membrane enclosed cell, the method comprising:
   providing a sample comprising at least one membrane enclosed cell and at least particle suitable for the delivery of the DNA or RNA molecule out of a membrane enclosed cell organelle through heat induced release of said DNA or RNA molecule, the particle comprising
   a superparamagnetic core capable of generating heat in a magnetic alternating field encapsulated in a heat sensitive coating where to said DNA or RNA molecule substance and a membrane disruptive agent are associated, wherein said heat sensitive coating comprises a micelle like structure in direct contact with said core, wherein said micelle like structure is built up by at least one of hydrophobic molecule and at least one molecule containing both a hydrophobic and a hydrophilic moiety, wherein said hydrophilic moiety contains lipids,
   wherein the size of the superparamagnetic core is between 8 and 15 nm,
   wherein the particle is absorbed into the cell by endocytosis in the form of an endosome within the cell;
   applying a magnetic alternating field to said sample, whereby thermal energy of the particle core causes the heat sensitive coating of said particle to decompose, thereby releasing the DNA or RNA molecule and the membrane disruptive agent from the particle, wherein said magnetic field has an alternating field direction of a frequency in the range of 0.1 to 5 MHz;
   rupturing the endosome due to interaction of the membrane disruptive agent and the endosome membrane;
   wherein the DNA or RNA molecule is delivered into the cell cytoplasm and the genetic code and/or metabolism of the host cell is modified with the DNA or RNA molecule.

2. The method of claim 1, wherein said superparamagnetic core consists of magnetite, maghemite, ironoxidehydrate, ferrites of the general formula $MeOxFe_2O_3$ where Me is a bivalent metal selected from the group consisting of Co, Ni, Mn, Be, Mg, Ca, Ba, Sr, Cu, Zn, Pt, Al, Cr, Bi, and combinations thereof.

3. The method of claim 1, wherein said heat sensitive coating is attached to the DNA or RNA molecule and membrane disruptive agent with single or multiple disulfide bonds, peroxide bonds or azo bonds or combinations thereof.

4. The method of claim 1, wherein a cell surface recognition molecule is also associated to the heat sensitive coating.

5. The method of claim 4, wherein said cell surface recognition molecule is chosen from the group consisting of antibodies, fragments of antibodies and lectins.

6. The method of claim 1, wherein said membrane disruptive agent is chosen from the group consisting of detergents, cholesterol, hydrophobic proteins and surfactants and mixtures thereof.

7. The method of claim 1, wherein said magnetic field has a field strength in the range of 1 to 100 mT.

8. The method of claim 7, wherein said magnetic field is exposed repeatedly as a series of pulses over time with each pulse duration between 1 and 600 seconds.

* * * * *